(12) United States Patent
Halahmi

(10) Patent No.: US 9,762,233 B2
(45) Date of Patent: Sep. 12, 2017

(54) SYSTEM FOR A CONTACTLESS CONTROL OF A FIELD EFFECT TRANSISTOR

(76) Inventor: Erez Halahmi, Gorgier (CH)

( * ) Notice: Subject to any disclaimer, the term of this patent is extended or adjusted under 35 U.S.C. 154(b) by 0 days.

(21) Appl. No.: 14/238,846

(22) PCT Filed: Jul. 31, 2012

(86) PCT No.: PCT/IB2012/053917
§ 371 (c)(1),
(2), (4) Date: Feb. 14, 2014

(87) PCT Pub. No.: WO2013/024386
PCT Pub. Date: Feb. 21, 2013

(65) Prior Publication Data
US 2014/0197877 A1 Jul. 17, 2014

Related U.S. Application Data

(60) Provisional application No. 61/524,233, filed on Aug. 16, 2011.

(51) Int. Cl.
*H03K 17/16* (2006.01)
*H03K 17/94* (2006.01)
*G01N 27/414* (2006.01)
*H01L 29/78* (2006.01)

(52) U.S. Cl.
CPC ........... *H03K 17/94* (2013.01); *G01N 27/414* (2013.01); *H01L 29/78* (2013.01)

(58) Field of Classification Search
CPC ... H01L 27/15; H01L 27/11521; G11C 16/10; G11C 16/0483; B82Y 10/00
See application file for complete search history.

(56) References Cited

U.S. PATENT DOCUMENTS

| | | | | |
|---|---|---|---|---|
| 5,401,035 A | * | 3/1995 | Schoenmaekers | A01C 7/046 111/185 |
| 6,618,866 B1 | * | 9/2003 | Edmondson | E03D 5/00 4/321 |
| 2003/0066793 A1 | * | 4/2003 | Cluggish | H01J 49/28 210/222 |
| 2005/0167575 A1 | * | 8/2005 | Benz | H01J 31/26 250/214 VT |
| 2007/0099173 A1 | * | 5/2007 | Spira | B82Y 10/00 435/4 |
| 2009/0263641 A1 | * | 10/2009 | Martin, III | B05D 1/60 428/221 |
| 2011/0133783 A1 | * | 6/2011 | Glass | H03M 1/204 327/72 |

* cited by examiner

*Primary Examiner* — Sibin Chen

(57) ABSTRACT

The invention stems from the realization that it is possible to control the electric field in the gate region of a field effect transistor (MOS, FET etc.) without changing the net charge of the gate electrode or without resorting to electrical conduction. According to an aspect of the invention, the electric field is changed by modifying the charge distribution within the gate electrode without materially adding or subtracting charge carriers to it or changing its net charge. This is achieved by displacing one or more sources of electric field, for example free charges, or conductive or non-conductive surface charges in the proximity of the gate electrode. By electric induction, the electric field produce a separation of charges in the gate electrode and an alteration in the conduction state of the FET transistor.

5 Claims, 3 Drawing Sheets

SYSTEM FOR A CONTACTLESS CONTROL OF A FIELD EFFECT TRANSISTOR

REFERENCE DATA

This application is a continuation of U.S. provisional application 61/524,233 filed on 16 Aug. 2011, the contents whereof are hereby incorporated.

FIELD OF THE INVENTION

Embodiments of the present invention relate to a method of interfacing an electronic device, like for example a transistor, a CMOS field effect transistor, or other electronic devices without a direct material contact with it.

DESCRIPTION OF RELATED ART

Field effect transistors in general and CMOS transistors in particular are very commonly used today either as components or in an integrated circuit. The way they are controlled is by modifying the field applied to the control leg of it, usually called "gate". This change of field is achieved by modifying the voltage applied to the gate. In the present application, for the sake of simplicity, reference will be made to CMOS field-effect transistor, but it must be understood that the method of the invention applies likewise to JFET, HEMFET, and other active electronic devices.

In some applications, like for example US20070063304 a FET transistor state is changed by modifying directly its gate voltage by a conductor path materially connected with it. In such cases, that are the vast majority, the control of the transistor relies on a conductive link to transfer charge to the gate, and hence modify its voltage level.

Floating gate transistors are also known, among others from U.S. Pat. No. 7,193,264. In this example a floating gate MOS transistor with one or more control gate is constructed. In these devices, however, net gate charge is changed by a capacitor-coupled circuit, so that even those device rely solely on electrical conduction involving the motion of charge carriers in solids.

Such control methods, despite being extremely widespread and successful, present nevertheless some limitations. In particular, every change of logical state of a conductor correspond to a small dynamic current that must be supplied by the power source. In high-speed digital circuits, such dynamic currents can add-up to considerable values. Dynamic currents are particularly strong in connection systems, for example connection buses between processors or processor subsystems, because of their relatively high capacity.

This problem is especially relevant in microprocessors like CPUs where billions of transistors and several cores are interconnected. These interconnections add large capacitance to the gate of the receiving transistors and therefore require a lot of energy to change state at the high clock rates that are requested. It is estimated that interconnections are responsible for up to 50% of energy used in the last generation of CPUs and are also responsible for about half of the delays in time critical paths.

It is perceived that the constant increase of the power spent in the interconnections is an important limiting factor in the rise of performances of microprocessors, and that a system of controlling electronic devices and interconnecting electronic devices between them that does not present this high level of power consumption and dynamic currents would lend to the realization of faster and more efficient digital processors.

BRIEF SUMMARY OF THE INVENTION

It is an aim of the present invention to propose a method of controlling a FET transistor that overcomes the limitations of the prior art, and this is achieved by the object of the appended claims.

The invention stems from the realization that it is possible to control the electric field in the gate region of a field effect transistor (MOS, FET etc.) without changing the net charge of the gate electrode or without resorting to electrical conduction. According to an aspect of the invention, the electric field is changed by modifying the charge distribution within the gate electrode without materially adding or subtracting charge carriers to it or changing its net charge. This is achieved by displacing one or more sources of electric field, for example free charges, or conductive or non-conductive surface charges in the proximity of the gate electrode. By electric induction, the electric field produce a separation of charges in the gate electrode and an alteration in the conduction state of the FET transistor, as it will be seen further on.

The greatest advantage of such an approach is that it reduces the capacitance connected to the gate and therefore the energy required to modify the state of the transistor.

According to one aspect of the invention, the source of electric field that can be free electrons and/or free ions and/or free charged particles that move in an essentially evacuated space from a source electrode to a target electrode and, when impinging on the target, provide a field source that is used to drive the FET. Preferably the electrons or charged particles are confined in a vessel with walls at least in part realized by a Negative Electron Affinity (NEA) material.

In a variant realization, the charged particles are confined in an evacuated vessel with walls at least partly realized with $SiO_2$, or an equivalent material, and has been 'activated' by storing an amount of electrons, and/or charged particles, in its interior, as it will be seen further on.

According to another aspect, the source of electric field is a beam of electrons or ion that move in an evacuated space along ballistic trajectories or bounce inside in a vessel with walls at least in part realized by a Negative Electron Affinity (NEA) material or activated $SiO_2$. A beam of electron going near a gate of a CMOS transistor will again change the charge distribution on it and therefore the channel between its source and its drains and therefore the current that can go through it. The CMOS transistor being controlled may be a part of an integrated circuit as well and the same charge can control one or more of them on the IC.

According to another aspect of the invention, the source of electric field could be charges bound to an electrified material or a charged conductor that is moved without adding or subtracting charges to it. For example an electrified rod that is moved in close relationship with the transistor that is desired to control. As the rod gets closer to the gate of the transistor, the charge distribution on the gate changes causing a change in the voltage and or the current going through the transistor.

BRIEF DESCRIPTION OF THE DRAWINGS

The invention will be better understood with the aid of the description of an embodiment given by way of example and illustrated by the figures, in which:

FIG. 1A is illustrating in a self-explanatory manner an example of a CMOS transistor of N-channel type whose state is "OFF", no channel is formed and no current can pass. FIG. 1B is illustrating in a self-explanatory manner an example of a CMOS transistor of N-channel whose state is "ON", when channel is formed and a current can pass, without changing the net charge on its gate.

DETAILED DESCRIPTION OF POSSIBLE EMBODIMENTS OF THE INVENTION

Figure 1A:
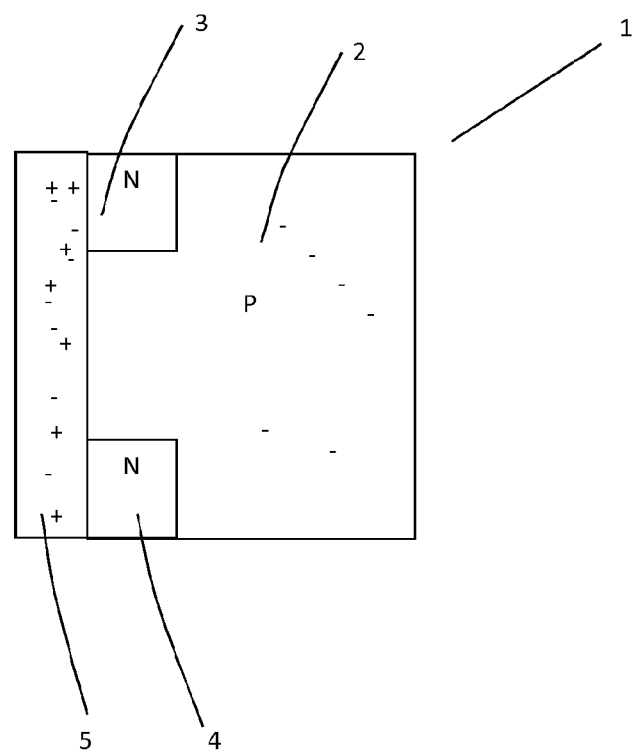
FIGS. 1A and 1B illustrate a specific, but not limiting examples of the invention.
Figure 1B:
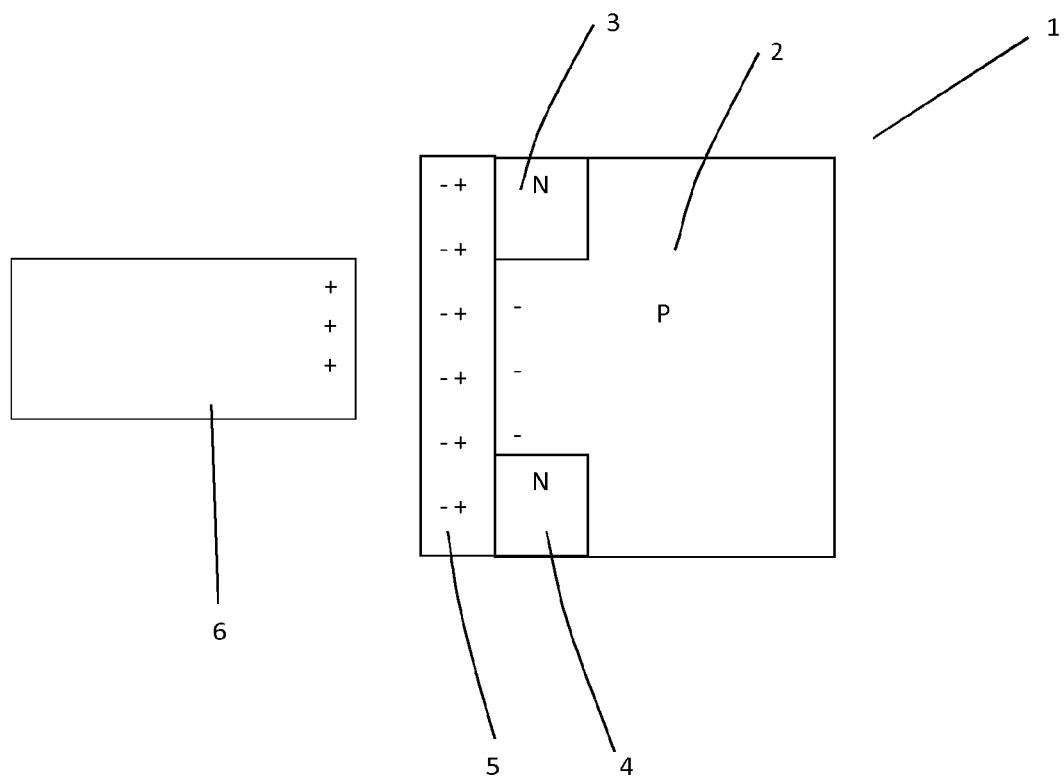

Referring to FIG. 1A, a CMOS transistor 1 of N channel type has a source 3 of N type, a drain 4 of N type, and a substrate 2 of P type. Some electrons are distributed randomly on the substrate 2 and on the gate 5 so a channel does not exist and there is no passage between the source 3 and the drain 4, so the transistor 1 is at OFF state (no current can pass at either direction). Referring to FIG. 1B, a CMOS transistor 1 of N channel type has a source 3 of N type, a drain 4 of N type, and a substrate 2 of P type. A 5 stick that is charged positively 6 is brought to the proximity of the gate 5 and attracts the negative charges in the gate 5. As a result a positive charge goes to the opposite side of the gate 5 and attract the electrons on the substrate 2 which form a channel between the source 3 and the drain 4. This channel allows a current to flow between the source 3 and the drain 4 (in both directions) and the transistor is at "ON" state. The only difference 10 between the device in FIG. 1A and of FIG. 1B is the existence of a charge stick close to the gate. In both cases the change in the net charge on the gate remains essentially 0, or very close to 0. The stick 6 can be replaced by free space charged particles, ions, electrons etc. These particles can be either free, on, or inside any conducting, partially conducting, or non-conducting material. The gate 5 can have an additional layer (one or more) of conducting, partially conducting, or non-conducting material. The transistor 1 can be more than one controlled by the same input, stand alone or in an integrated circuit.

Figure 2:
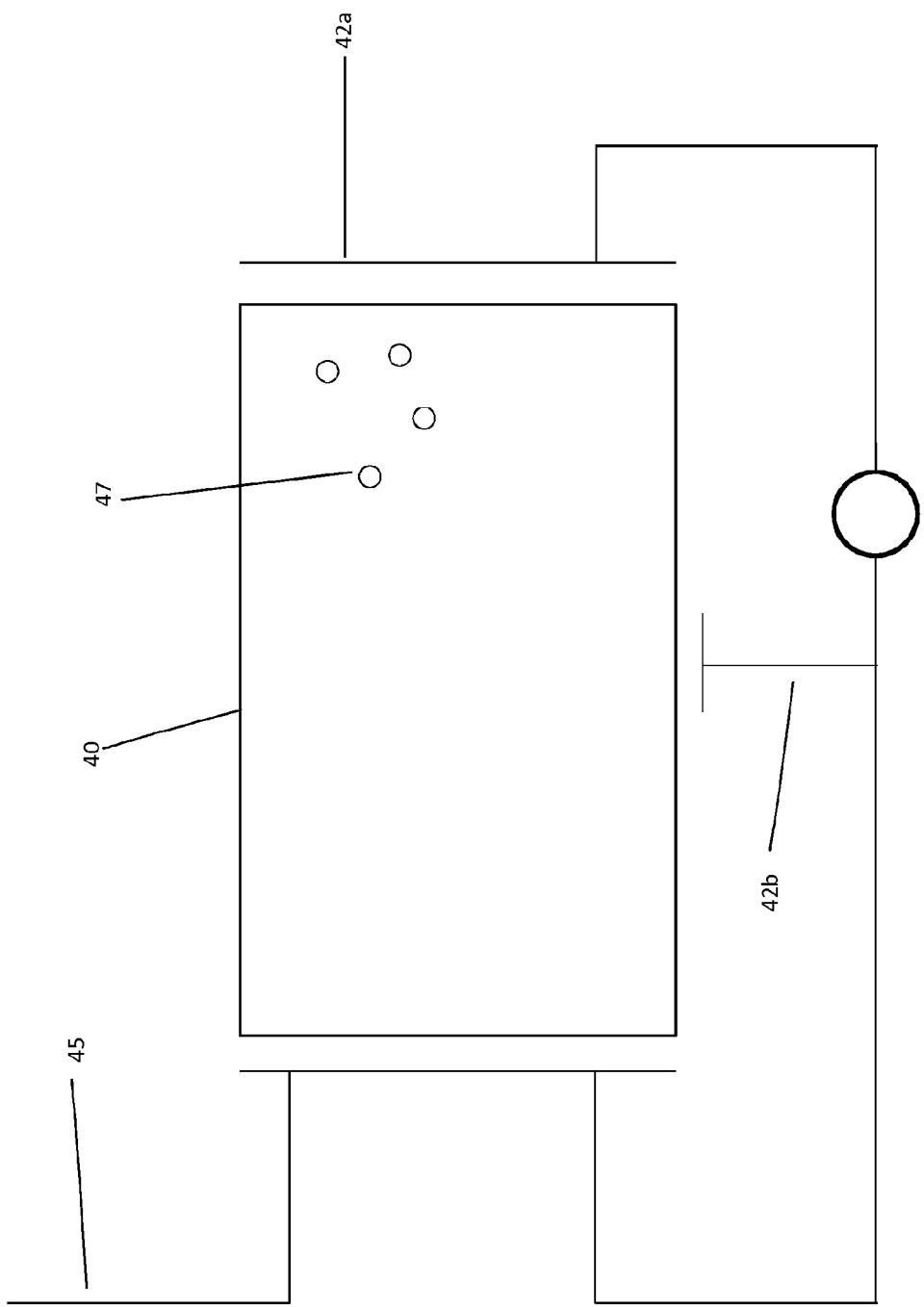
FIG. 2 illustrates an embodiment of the invention in which a transistor is controlled by means of electrons or charged particles contained in an evacuated vessel.

FIG. 2 shows schematically an embodiment of the present invention in which the FET is controlled by electrons that are guided in spatial proximity with its guide without energy losses. This variant of the invention has a tube 40 that is closed at its extremities by suitable caps and whose inner volume is evacuated. For the purpose of the present invention 'evacuated' means that the residual inner pressure is such that the electron's mean free path is at least equal, preferably much larger than, the greater dimension of the vessel.

Preferably, the vessel or tube 40 is made with walls that allow at least partially elastic scattering of the electrons. Polyethylene or Parylene (in thin film) are such materials, for example. Preferably one would select a material with a Negative Electron Affinity of at least 1.5 eV. This would allow elastic scattering of electrons up to about 1 eV kinetic energy. In alternative, the vessel 40 can be manufactured from $SiO_2$, or any suitable insulating material, that has been 'activated' by storing an amount of electrons, and/or charged particles, in its interior. The electrons can be generated in the vessel by photoelectric or thermoelectric emission, or by an electron gun, or any other suitable electron source. It has been observed that part of the stored charge fixes itself to the walls of the vessel, and part remains free. Upon the application of electric fields the free charge fraction can move in the vessel with little energy losses due to wall scattering.

The evacuated vessel with NEA or activated $SiO_2$ walls does not allow electrons to penetrate into the material as far as their energy does not exceed a certain threshold and, therefore, it can be considered an electron guide. If the vessel is loaded with an amount of free electrons 47 prior to its sealing, the charges will remain freely mobile for a very long time, and would travel within the tube, bouncing at least partially elastically on the walls, according to external electric fields. The tube acts therefore as a 'field conductor', similarly to a conductive material, but without introducing capacitive effects and dynamic current losses.

Returning to FIG. 2, one extremity of the tube comprises a transmitting unit that comprises means to attract or repel the free charges pre-loaded in the tube. This can be made, for example by applying a voltage difference between acceleration electrode 42a and reference electrode 42b, such that the free electrons in the vicinity of the transmitter unit are accelerated towards the other end of the tube.

At the extremity of the tube opposite to the transmitting unit, a FET transistor 45 coupled to the inner tube's volume, either directly, as illustrated or by a suitable arrangement of electrodes. The electron coming from the transmitting unit create an electric field in the FET's active volume and change the voltage at its terminals or the current flowing though the FET.

In a preferred example, the gate of the FET 45 will be pre-charged, for example by connecting it for a moment to a source of positive voltage, and then left floating, so that the positive charge accumulated on the gate will bring and keep the FET in conduction. The electrons coming from the transmitting unit 42a-b will discharge the gate and bring the FET in the inactive state.

The vessel itself can be straight or curved, according to the structure of the interconnection required. Moreover, a single transmitter can be coupled, by one evacuated vessel, to several receiving devices.

The invention claimed is:

1. A device for controlling a Field Effect Transistor, the device comprising an evacuated vessel having first and second extremities, preloaded with charge carriers creating free charges and having walls on which the free charges can scatter at least partially elastically, the first extremity being operable as a chargeable element by which said device faces a gate region of the Field Effect Transistor being spaced from and located in proximity of the gate region, and the second extremity having transmitter means configured and operable to accelerate the free charges in said evacuated vessel towards the first extremity, effecting a change of an electric field in said space between the first extremity and the gate region causing separation of charges in the gate region by electric field induction and modification of the charge distribution in the channel of the transistor, thereby modifying a conduction state of the transistor in a contactless manner.

2. The device of claim 1, wherein the charge carriers are electrons and the evacuated vessel has the walls exhibiting negative electron affinity of 1.5 eV or higher, applied between the free charges and the walls.

3. The device of claim 1, wherein the evacuated vessel comprise polyethylene or parylene or $SiO_2$ applied between the free charges and the walls.

4. An electronic device comprising:
   a Field Effect Transistor comprising source and drain electrodes with a channel between them, and a gate region; and a controller configured and operable to controllably vary conduction state of the transistor, wherein the controller is spaced-apart from the gate region, and has a chargeable element by which it faces the gate region and which is located in a proximity of the gate region, such that a charge on said chargeable element creates an electric field in a space between the chargeable element and the gate region, causing separation of charges in the gate region by electric field induction and modification of the charge distribution in the channel of the transistor, thereby controlling alteration in a conduction state of the transistor.

5. The electronic device of claim 4, wherein said controller comprises an evacuated vessel having first and second extremities, preloaded with free charges and having walls on which the free charges can scatter at least partially elastically, the first extremity operating as the chargeable element spaced from and in proximity of the gate region, and the second extremity being configured and operable, by an electric circuit, to accelerate the free charges in said evacuated vessel towards the first extremity, such that the free charges affect a change in the electric field in said space between the first extremity and the gate region and modify the conduction state of the transistor.

* * * * *